United States Patent [19]
Blyler, Jr. et al.

[11] Patent Number: 5,076,096
[45] Date of Patent: Dec. 31, 1991

[54] MOLDING OF THERMOSET MATERIALS

[75] Inventors: Lee L. Blyler, Jr., Basking Ridge; Philip Hubbauer, Clark; Gerhard W. Poelzing, New Providence; Richard C. Progelhof, Berkeley Heights, all of N.J.

[73] Assignee: American Telephone and Telegraph Company, AT&T Bell Laboratories, Murray Hill, N.J.

[21] Appl. No.: 301,938

[22] Filed: Jan. 25, 1989

Related U.S. Application Data

[62] Division of Ser. No. 948,436, Dec. 24, 1986, abandoned, Ser. No. 690,417, Jan. 10, 1985, abandoned, and Ser. No. 485,857, Apr. 18, 1983, abandoned.

[51] Int. Cl.⁵ ............................................. G01N 11/08
[52] U.S. Cl. .......................................................... 73/55
[58] Field of Search ........................................ 73/55, 56

[56] References Cited

U.S. PATENT DOCUMENTS

| 3,203,225 | 8/1965 | Sieglaff et al. | 73/56 X |
| 4,213,747 | 7/1980 | Friedrich | 73/55 X |
| 4,425,790 | 1/1984 | Bice et al. | 73/55 |

FOREIGN PATENT DOCUMENTS

| 1207559 | 7/1986 | Canada | 73/55 |
| 1916162 | 10/1970 | Fed. Rep. of Germany | 73/56 |
| 21542 | 2/1983 | Japan | 73/56 |
| 1346975 | 10/1987 | U.S.S.R. | 73/56 |

Primary Examiner—John Chapman
Assistant Examiner—Joseph W. Roskos
Attorney, Agent, or Firm—Bruce S. Schneider

[57] ABSTRACT

Various methods have been proposed for measuring the viscosity of thermosetting polymers. It has been found that these method are generally inaccurate. A test which avoids the inaccuracies of previous techniques is proposed. In this test the heated thermosetting resin is forced at a known flow rate through a runner and through a capillary tube at the end of the runner. By measuring the pressure differential across the capillary a meaningful measure of viscosity is obtained.

14 Claims, 2 Drawing Sheets

MOLDING OF THERMOSET MATERIALS

This is a division of application Ser. No. 948,436 filed Dec. 24, 1686, and Ser. No. 690,417 filed Jan. 10, 1985, and Ser. No. 485,857 filed on Apr. 18, 1983, all now abandoned.

BACKGROUND OF THE INVENTION

1. Field of the Invention

This invention relates to the molding of an organic material and, in particular, to the molding of thermosetting polymers.

2. Art Background

Compositions denominated thermosetting resins are employed in a wide variety of products. For example, to provide protection thermosetting resin compositions (e.g., a novolac epoxy polymer or a cresol-novolac epoxy polymer either one combined with a phenol novolac or cresol-novolac hardener) are molded to encapsulate integrated circuit chips and their associated electrical leads. Generally to accomplish this encapsulation, a multi-cavity mold is employed to simultaneously process a large number, e.g., seventy or more, integrated circuits. These molds separate into halves and generally include (1) a common area for introducing the thermosetting resin, (2) channels, i.e., runners, which each run from the common area and which each provide access to one or more, (3) gates that open into (4) mold cavities. In the example of the simultaneous encapsulation of a plurality of chips, each chip and its associated electrical leads and connections are placed in a separate cavity, the mold is heated, thermosetting resin preheated to a temperature below the mold temperature is introduced into a reservoir, and pressure is applied to force the material (1) from the reservoir to the mold common area and (2) through the runners to the gates. This pressure is maintained until the cavities are filled and the resin has cured. To achieve an economical production rate, the entire mold-filling sequence is generally performed in from 10 to 30 seconds. After a suitable residence time to complete the curing reaction, e.g., 2 to 4 minutes, the mold is split and the molded objects, e.g., the encapsulated chips, are removed.

The viscosity of the resin strongly influences the molding procedure. If the thermosetting resin is too viscous at molding temperatures, it cannot be forced through the runners and gates without the use of a relatively high pressure. However, the use of relatively high pressures often has significant adverse effects. For example, in the case of electronic components, if a relatively high pressure is employed, the force of the polymer exerted on the contents of the cavity is often sufficient, for example, to damage the electrical connections to the integrated circuit.

It is generally believed that during nominal molding filling times resin viscosity does not substantially vary and remains at a level where a nominal pressures at the gate are produced. To determine a suitable molding pressure for a particular thermosetting resin and its associated viscosity, a spiral flow test is generally utilized. (See, for example, American Society for Testing Materials, Test D3123 described in *ASTM Standards*, Part 35.) In such a test, a mold having a spiral runner pattern but no gates or cavities is employed. The mold is heated to a typical molding temperature, e.g., to a temperature in the range 150 to 180 degrees C., and the resin is forced at a predetermined pressure through the spiral runner until, due to curing, it solidifies. The distance along the spiral that is traversed is considered to be a measure of the viscosity of the resin, and through empirical results, is related to a suitable molding pressure. The flow time in the spiral is similarly related to the time for gelation. Although molding procedures determined through the spiral flow test lead to acceptable yields for molded products, such as molded electronic components, improved yield is certainly desirable.

SUMMARY OF THE INVENTION

It has been found that the viscosity of thermosetting materials in a mold changes rapidly within the time frame associated with molding procedures. In particular, two significant effects have been observed. Firstly, the thermosetting resin composition preheated to a temperature below the mold temperature quickly approaches the temperature of the mold upon entering the common area and runner system. This effect causes the viscosity of the material to decrease at a substantial rate soon after its introduction into the common area and runner system of the mold. This reduction in viscosity is progressively offset by an increasing augmentation of viscosity due to the curing of the resin begun by heating. Thus, a second effect is observed. The viscosity of the thermosetting resin reaches a short-lived minimum. Most significantly this minimum occurs typically within the mold-filling time period. Beyond this minimum the resultant viscosity increases rapidly with time again due to the continued curing of the resin. If the resin is preheated rapidly and molding is immediately initiated, the difference between the viscosity minimum observed and the viscosity of the unreacted resin at the mold temperature is relatively small, i.e., typically the minimum viscosity is only about 10 to 30 percent greater. Thus, observation of these two effects has allowed the modification of molding procedures and related techniques to advantageously improve the molded product especially for thermosetting resins which reach the gel point within 30 seconds of transfer into the mold and most especially for those which reach the gel point within 25 or 20 seconds. (See P. J. Flory, *Principles of Polymer Chemistry*, p. 47, Cornell University Press, Ithaca, 1953 for a definition of gel point and *ASTM*, Part 36, D 2765 for a means of measuring the gel point.) In particular, improvement in the result obtained in molding these resin compositions is achievable by modifying the molding procedure so that the thermosetting resin composition reaches the gates at a viscosity which is close to its viscosity minimum, i.e., at a viscosity no greater than 1.3 times the viscosity of the unreacted resin at the mold temperature. As discussed, the viscosity of the resin as it enters the gate depends on the molding conditions. Therefore, parameters such as runner length, runner geometry, and gate geometry are adjusted to satisfy this viscosity minimum condition. Additionally, it has been found that due to the two observed effects, spiral flow measurements are inadequate for determining the suitability of materials and for determining advantageous molding conditions. A technique which more closely reproduces the molding environment is employed to obtain a measure of viscosity which allows the appropriate modification of the molding procedure.

DETAILED DESCRIPTION

Figure 1:
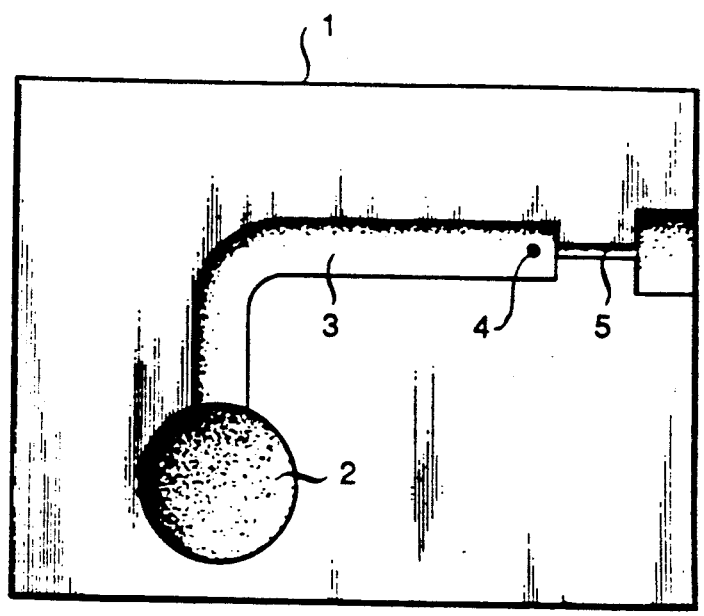
FIG. 1 is illustrative of one half a mold body suitable for making measurements in the practice of the invention.
Figure 2:
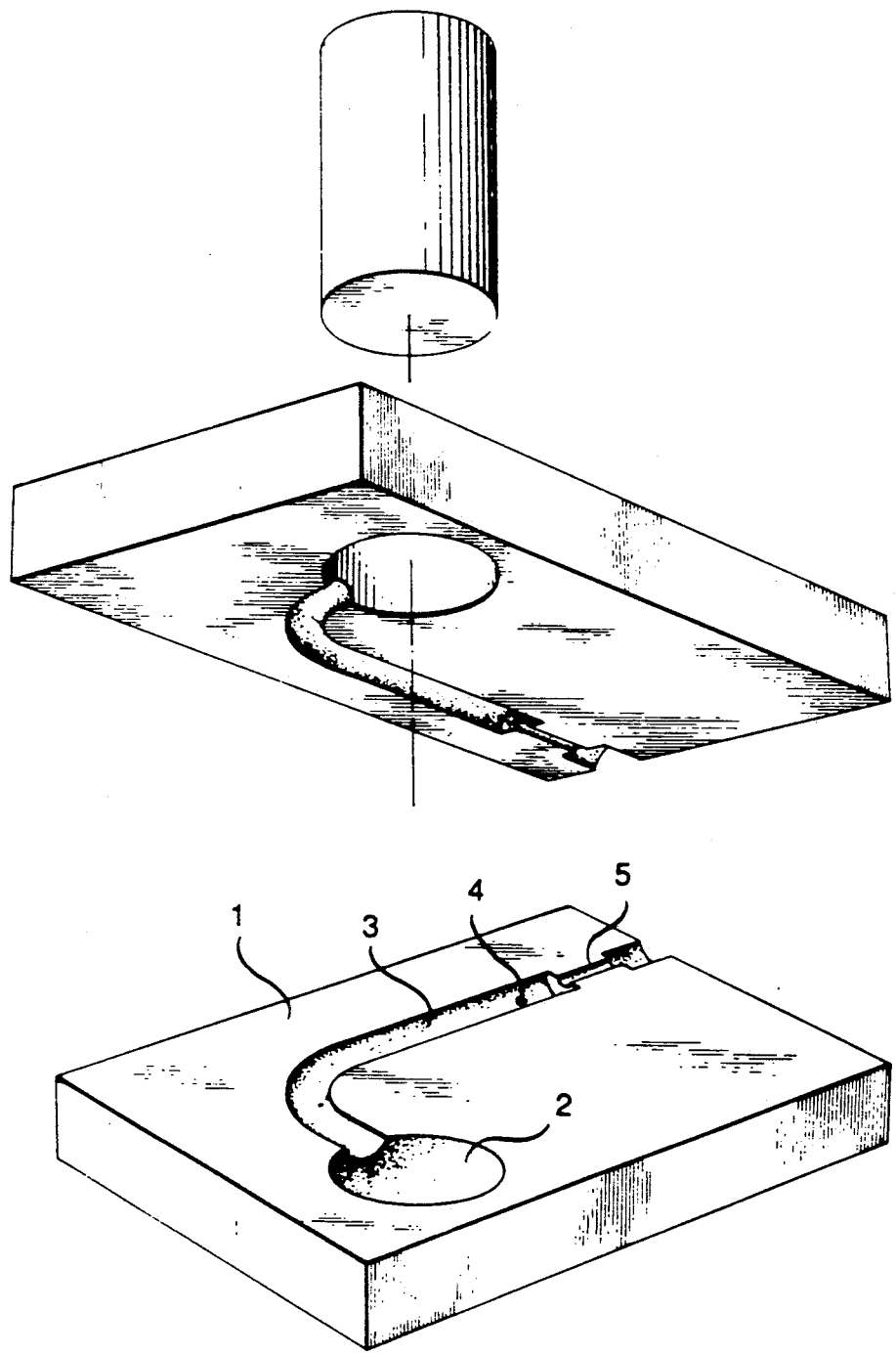
FIG. 2 is illustrative of a mold and means for introducing material through the mold together useful for making measurements in the practice of the invention.

As discussed, the invention involves the modification of typical molding procedures so that a thermosetting composition (a composition which undergoes a curing reaction upon heating) enters the mold cavities through their gates at a viscosity significantly lower than is generally achieved. To achieve this goal, it is appropriate to measure the viscosity of the thermosetting composition in a specific manner. In particular, a viscosity measuring device is employed which includes a reservoir, a runner, and a capillary region at the end of the runner. For example, a test mold, 1, such as shown in the Figure is employed. (The Figure shows one half of the mold since after each run the cured resin must be removed by splitting the mold.) By forcing a heated thermosetting resin at a known flow rate through the runner, 3, and capillary, 5, and by measuring the pressure differential across the capillary, a meaningful measure of viscosity is obtainable.

The capillary region, 5, should have an opening with a cross-section in the range 0.01 $cm^2$ to 0.20 $cm^2$ and should have a length in the range 1 cm to 10 cm and preferably should be essentially cylindrical in cross-section. Larger cross-sections and shorter lengths do not present a sufficient resistance to the flow of the thermosetting resin and, therefore, do not present a pressure differential which is easily measured. Additionally even if measurement is possible, larger cross-sections typically lead to inaccurate results. Smaller cross-sections and greater lengths provided too large a resistance to the thermosetting resin and substantially impede flow. Conventional means for measuring the pressure difference across the capillary region are utilized. For example, a pressure transducer or a pin of known diameter contacting a force transducer is positioned at point 4 in the Figure to monitor the pressure differential. (Generally pressure differentials in the range 50 to 2000 psi are easily measured.) For the viscosity determination, the volumetric flow rate of the thermosetting resin is also measured. Preferably by utilizing a plunger, a force is applied to the thermosetting resin in a reservoir and by connecting the reservoir to the common area of the mold, the resin is forced through the runner and capillary. Preferably, the movement of the plunger is monitored with a position transducer and the time derivative of the plunger displacement is employed to yield the instantaneous volumetric flow rate of the resin. Alternatively, a velocity transducer is employable to measure the velocity of the plunger and thus yield the volumetric flow rate. For typical thermosetting resins, plunger pressures, i.e., driving pressures in the range 100 psi to 2500 psi are utilized and typically produce capillary pressure differentials in the range 50 to 2000 psi. Higher pressures generally force the resin between the test mold halves and cause measurement inaccuracies, while lower pressures are insufficient to force the materials through the runners and subsequently through the capillary region of the mold.

Two modes of measuring viscosities for the purpose of adjusting the molding procedure are advantageously employed. In the first mode, an isothermal technique is utilized. In particular, a series of viscosity measurements are taken to determine the variation of viscosity of a resin with time for each of a variety of temperatures and driving pressures. These isothermal measurements are performed by heating the mold and the reservoir to a temperature within the range in which the viscosities are to be determined. The thermosetting resin is also rapidly heated (typically 10 to 30 seconds) to the same temperature using conventional techniques such as dielectric heating. (Dielectric heating procedures are well known and are described in *The Encyclopedia of Plastics Equipment*, H. R. Simonds, ed., New York: Reinhold Publishing Corp., 1964.) The preheated thermosetting resin is then placed in the heated reservoir and is forced through the mold by applying a driving pressure by, for example, utilizing a plunger in the reservoir. Since the thermosetting resin, the reservoir, and the mold are all at the same temperature, the entire experiment is, thus, carried out essentially isothermally. (The temperature is not substantially affected by effects such as viscous drag and exothermic curing reactions.)

For each measurement, and thus for each temperature and driving pressure, the volumetric flow rate of the resin and the pressure difference across the capillary tube are measured as they vary with time. Viscosity as a function of time is then determined from these measurements utilizing the Hagen-Poiseuille equation. (The Hagen-Poiseuille equation is well known and is extensively described in references such as J. R. Van Wazer et al, *Viscosity and Flow Measurement*, New York: Interscience Publishers, 1963 and Z. Tadmor et al, *Principles of Polymer Processing*, New York: John Wiley and Sons, 1979.) The variables in the Hagen-Poiseuille equation are the viscosity, the volumetric flow rate, the pressure differential, the capillary radius and the length of the capillary. Thus, the viscosity, the only unknown variable, is determined from the previously described measurements. However, the Hagen-Poiseuille equation is based on a Newtonian resin viscosity, i.e., a viscosity which is independent of the resin shear rate. (Shear rate is the change of flow velocity of the resin with radial position across the capillary.) This basis is acceptable for purposes of adjusting the molding procedure in accordance with the invention since the correction for dependence of shear rate is relatively small and since it is still possible to treat the viscosity for this measurement as dependent on flow rate. Without correction the viscosity is, in fact, an apparent viscosity suitable for determining appropriate mold process parameters. However, if it is desired to obtain absolute viscosity values, the Rabinowitsch correction which is a well-known corrective method described in Van Wazer and Tadmor et al. supra should be applied. This correction is made by doing a series of runs at a given temperature and varying the shear rate by varying the driving pressure for each run. This procedure allows a determination of the dependence of viscosity on the shear rate by comparing the viscosity measured in each run at an equivalent time during the run.

Thus, as discussed through isothermal measurements if the pressure differential and the volumetric flow rate of the resin are monitored over a period of time, then by utilizing the Hagen-Poiseuille equation the viscosity variation with time at a given temperature is determined. (Through the Rabinowitsch correction the viscosity variation with shear rate is ascertained.) By repeating the procedure at various temperatures, the viscosity versus time and the viscosity versus shear rate relationships for each set of conditions are ascertained. On the basis of this information a constitutive equation which describes the viscosity of the resin as a function of time, temperature, and shear rate is generated.

To relate the viscosity information obtained using the isothermal procedure to the actual molding process, it is necessary to study the thermal profile of the resin as it flows through the mold which is ultimately to be utilized to mold objects. A resin temperature profile along each runner in the mold should be determined. (Resin temperatures at intervals of 4 cm are sufficient for purposes of this determination.) Resin temperatures along the runners are determined through conventional techniques. For example, temperature sensors such as melt-thermocouples are positioned along the runners to determine the temperature of the resin as it fills the runners and enters the molding cavities through the associated gates. By convoluting the resin temperature profile and the viscosity variation with time, shear rate, and temperature, the viscosity profile of the resin as it flows through the mold to be ultimately used in processing is ascertained.

In the first mode for determining viscosity variations with time as a function of temperature, an isothermal capillary technique is employed. In this technique, the length of the runner is not particularly significant. However, a second mode is available for making meaningful viscosity measurements and for allowing the adjustment of the molding process to satisfy the viscosity minimum requirement. This technique is not isothermal and employs a runner whose configuration and cross-section are approximately equivalent to those ultimately to be utilized in the actual molding operation. (If a plurality of runners are involved in the molding operation, a viscosity determination for each runner, individually, is preferably performed.) In this second measuring technique, the reservoir and the test mold are held at the temperature to be employed in the actual molding operation. The molding resin is preheated to a temperature lower than the mold temperature, e.g., 50 to 100 degrees C. lower. The same conditions as those to be employed in actual molding are utilized except the material at the end of the runner flows through a capillary instead of a gate. For example, the driving pressure to be employed in the molding process is also utilized. The volumetric flow rate and the pressure differential across the capillary are measured as a function of time. The temperature of the resin is also measured in the vicinity of the capillary. Through the Hagen-Poiseuille equation the viscosity of the thermosetting resin which would, during molding, arrive at the gate is determined. Thus in this second technique, the viscosity of the resin which flows through the gate under mold conditions is measured directly. (Although it is possible to make the Rabinowitsch correction to the non-isothermal viscosity data, it requires a series of isothermal runs, such as those described earlier. While the use of the correction is scientifically more rigorous and is not precluded, generally it is not required for adjusting the molding process according to the invention. In addition, thermal gradients across the radial direction of the capillary tube introduce some inaccuracy in the results but are generally negligible.)

As previously discussed through such determinations, the applicants have found that thermosetting materials rapidly approach the molding temperature and undergo a viscosity minimum within times typically required to fill the molding cavities. To take advantage of these observations, the molding parameters should be adjusted so that the viscosity of the material when it enters the cavities through their gates is within 30 percent of the viscosity of the unreacted composition at the mold temperature. The viscosity of the unreacted composition at the mold temperature is determined utilizing the previously described isothermal measurement technique. First, a series of viscosity measurements with time are done for each of at least three temperatures by varying the drive pressure for each run of each series. Each resulting curve is extrapolated to zero time to attain the zero time viscosity at a particular shear rate. (Zero time is the time the rapidly heated composition first reaches the test temperature.) For each temperature, zero time viscosity versus its corresponding shear rate is plotted resulting in one curve for each temperature. One shear rate is chosen, and the viscosity at this shear rate for each temperature is determined from the viscosity versus shear rate plot. Each of these ascertained zero time viscosities at a chosen shear rate is then plotted as a log viscosity versus the reciprocal of the corresponding absolute temperature. An extrapolation to the mold temperature yields the viscosity of the unreacted resin composition at this temperature. (Unreacted in this context is the reaction state of the resin before heating.) To satisfy the viscosity minimum requirement, for example, the geometry of the runners, the pressure applied to force the material through these runners, the geometry of the gates, and the mold temperature are adjustable. Such molding process parameters are adjusted using a controlled sample and using the viscosity and temperature determination techniques previously discussed to yield the desired configuration and to satisfy the minimum viscosity criterion. In contrast, use of viscosity data measured by the spiral flow technique yields data which in no way describes the viscosity behavior of thermosetting resins during molding. It is only through a measurement involving a mold containing a capillary and not through the conventionally employed spiral flow method, that sufficiently accurate information is obtainable to adjust molding parameters and to satisfy the viscosity criterion of the inventive molding process.

What is claimed is:

1. An apparatus for measuring the viscosity of a thermosetting composition comprising a reservoir with means for applying a force to the contents of said reservoir, a mold comprising a common area with means for communicating with said reservoir, a runner from said common area to a capillary area, means for measuring a pressure across said capillary area, and means for measuring the volumetric flow rate of said composition through said mold.

2. The apparatus of claim 1 wherein said means for measuring said pressure across said capillary area comprises a pressure transducer or a force transducer.

3. The apparatus of claim 1 wherein said capillary area has a length in the range 1 to 10 cm and a cross-sectional area in the range 0.01 to 0.20 cm$^2$.

4. The apparatus of claim 1 wherein said means for measuring volumetric flow comprises a velocity transducer.

5. The apparatus of claim 1 wherein said means for applying a force comprises a plunger.

6. The apparatus of claim 1 wherein said means for measuring volumetric flow comprises a position transducer.

7. A process for measuring the viscosity of a thermosetting composition comprising the steps of rapidly heating said resin, forcing said heated composition through a heated mold, said mold comprising a runner and a capillary area, determining the volumetric flow of said composition, and determining the pressure differential of said composition across said capillary area.

8. The process of claim 7 wherein said composition and said mold are heated to essentially the same temperature.

9. The process of claim 7 wherein said capillary area has a length in the range 1 to 10 cm and a cross-sectional area in the range 0.01 to 0.20 cm$^2$.

10. The process of claim 7 wherein said resin is forced through said mold by utilizing a plunger.

11. The process of claim 10 wherein said volumetric flow rate is determined by measuring the velocity or position of said plunger.

12. The process of claim 11 wherein said pressure differential is determined by utilizing a pressure transducer.

13. The process of claim 7 wherein said pressure differential is determined by utilizing a pressure transducer or a force transducer.

14. The process of claim 7 wherein said resin comprises a novolac-epoxy resin composition.

* * * * *